United States Patent [19]
Barton et al.

[11] 3,954,980
[45] May 4, 1976

[54] CHEMICAL COMPOUNDS

[76] Inventors: Derek Harold Richard Barton, c/o Department of Chemistry, Imperial College, London, S.W.7, England; Robert H. Hesse, c/o Research Institute for Medicine and Chemistry Inc. 49 Amherst St., Cambridge, Mass. 02142

[22] Filed: July 6, 1973

[21] Appl. No.: 376,961

Related U.S. Application Data

[63] Continuation of Ser. No. 190,633, Oct. 19, 1971, abandoned.

[52] U.S. Cl. .................... 424/241; 260/239.55 R
[51] Int. Cl.² .......................................... C07J 71/00
[58] Field of Search ................. 424/241; 260/239.55

[56] References Cited
FOREIGN PATENTS OR APPLICATIONS
941,140  11/1963  United Kingdom ........ 260/239.55 R

*Primary Examiner*—Elbert L. Roberts
*Attorney, Agent, or Firm*—Bacon & Thomas

[57] ABSTRACT

A method of contraception which comprises orally administering steroidal 11, 19-hemiacetals of 11-hydroxy-19-oxo compounds to human beings.

6 Claims, No Drawings

CHEMICAL COMPOUNDS

This is a continuation of application Ser. No. 190,633, filed 10/19/71, now abandoned, which is in turn a continuation of Ser. No. 14,802, filed 3/2/70, now abandoned, which is in turn a continuation of Ser. No. 747,827, filed 7/26/68, now abandoned, which in turn is a division of Ser. No. 514,691 filed 12/17/65, now abandoned.

This invention concerns novel steroids having contraceptive activity and a process for their preparation.

Many of the oral contraceptive steroids previously proposed, particularly those which occur naturally, give rise to unwanted side effects such as weight increase and salt and water retention. We have now found that certain steroid hemiacetals, which are more precisely defined hereinafter, are suitable for use as oral contraceptives and substantially avoid the above disadvantages. These substances are also useful steroidal aldosterone blockers.

According to the present invention we provide steroid hemiacetals of the skeletal formula

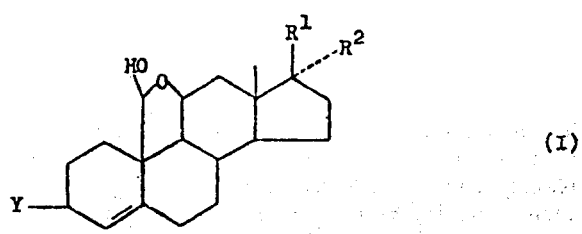

(I)

where Y is a ketone oxygen atom or represents a grouping convertible thereto, $R^1$ is a group $COCH_2X$, where X is a hydrogen or halogen atom, and $R^2$ is a hydrogen atom or an acyloxy group or $R^1$ is a hydroxy group and $R^2$ is an aliphatic group which may, if desired, carry one or more halogen atoms as substituents, the molecular weight of the steroid being at least 325 when $R^2$ is hydrogen.

The steroid hemiacetals according to the invention may carry other substituents, for example:
at the 6β-position : a halogen atom or an alkyl group
at the 9α-position : a halogen atom
at the 16-position : a methyl or methylene group or a halogenated methyl or methylene group or a halogen atom.

Where $R^2$ is an acyloxy group it is preferably a lower aliphatic acyloxy group having 1 – 6 carbon atoms e.g. an acetoxy or propionoxy group. $R^2$ may, for example, be a methyl, vinyl or ethynyl group or a vinyl or ethynyl group carrying an aliphatic substituent; such an aliphatic substituent may be saturated or may possess double or triple bonds and preferably possesses 6 carbon atoms. Thus, for example, $R^2$ may be a straight or branched lower alkenyl or alkynyl group e.g. a butadiynyl group. Where $R^1$ or $R^2$ or the 9α-position of the steroid carries a halogen atom this may be a fluorine, chlorine or bromine atom. In $R^1$ and $R^2$, fluorine or chlorine atoms are preferred and $R^2$, for example, may advantageously be a chlorovinyl group.

Where Y is a grouping convertible to a ketone oxygen atom, it may, for example, be a hydroxyl group or an acyloxy group such as acetyl. Those compounds in which Y is ketonic oxygen are preferred, however, for their activity as oral contraceptives.

As indicated above, the compounds according to the invention possess antifertility activity on oral administration which is substantially free from somatrophic effects leading to loss of libido, weight gain and water and salt retention. We have found that the related substance 17β-acetyl-19-oxo-androst-4-ene-11β-ol-3-one-11,19-hemiacetal, which we have described previously, also possesses activity of this kind although to a somewhat lesser extent.

According to a further, feature of the invention therefore, we provide pharmaceutical compositions containing one or more compounds according to the invention and/or 17β-acetyl-19-oxo-androst-4-ene-11β-ol-3-one-11,19-hemiacetal, together with one or more pharmaceutical carriers or excipients The active compounds in the compositions according to the invention thus comprise compounds of skeletal formula I wherein $R^1$ is a group $COCH_2X$, where X is a hydrogen or halogen atom, and $R^2$ is a hydrogen atom or an acyloxy group or $R^1$ is a hydroxyl group and $R^2$ is a vinyl or ethynyl group which may, if desired, carry one or more halogen atoms or aliphatic hydrocarbon groups as substituents.

The compositions according to the invention may take the form of oral, parenteral or rectal preparations. The preferred mode of administration is in oral formulations, for example, lozenges, tablets, capsules, dragees, and like dosage-unit forms as well as syrups, elixirs, emulsions, etc. The pharmaceutical carrier or excipient may, for example, be of the kind conventional for such formulations; e.g. starch, lactose, talc, magnesium stearate etc. in tablets, dragees and lozenges, gelatin for capsules and for the liquid preparations water or oil containing suspending, emulsifying, dispensing, thickening, flavouring agents etc.

Parenteral formulations will comprise the active steroid in solution or suspension in a parenterally acceptable liquid, for example sterile water, oils such as peanut oil or ethyl oleate, oily emulsions etc.

Rectal formulations will comprise a suppository base, for example a polyglycol or carbowax base.

The dosage unit forms of the compositions according to the invention preferably comprise 0.05 to 100 mg of active steroid, advantageously 0.1 to 50 mg. Units containing 1.0 to 25 mg are especially convenient.

Examples of useful dosage units are tablets for oral administration containing 2.5 or 25 mg of active substance.

The compositions will be administered at a daily dose level in the range 1 to 25 mg per day, for example 2 to 10 mg per day. The regimen may be as follows: (1) about 5mg/day, 20 days per cycle, (2) about 5mg/day for 3–5 days following ovulation, (3) about 5mg/day for 3–5 days following coitus, (4) 1–2 mg/day.

Advantageously, the compositions may contain a minor proportion of an oestrogenic or pro-oestrogenic substance, for example one of the compounds described in our pending cognate application Ser. No.

14317/64; 45811/64. There are also advantages in including a conventional progestational agent during the latter stage of monthly treatment in order to prepare the endometrium for the normal menstrual cycle.

The new compounds according to the invention may be prepared in any convenient way. According to a still further feature of the invention they may be prepared by selective hydrolysis of the oximino group of a compound of the skeletal formula

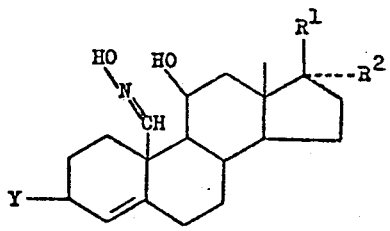

(where Y, R$^1$ and R$^2$ have the meanings given above) in ketoneprotected form where Y is ketone oxygen, followed if required by hydrolysis of the protected ketone group or groups.

The ketone-protected form of the compound of formula II may, for example, carry a ketal or thioketal group at the 3-position and, where R$^1$ is COCH$_2$X, the carbonyl group in the 20-position will also be in protected form, for example, in the form of a ketal or thioketal group. During the hydrolysis of the oximino group to form the required hemiacetal, the ketone-protecting groups will remain protected so that the 19-oxo group initially formed will cyclise spontaneously with the 11-hydroxy group without side reactions taking place. The hydrolysis of the oximino group is advantageously effected by the action of nitrous acid under weakly acid conditions e.g. using a soluble nitrite in the presence of a carboxylic acid such as acetic acid. The hydrolysis of the ketone-protecting groups may be effected using a mineral acid, e.g. hydrochloric, hydrobromic, sulphuric, perchloric or phosphoric acid.

According to a modification of the above process the starting oxime may carry substituents in the A-ring which on subsequent treatment yield the required Δ$^4$ structure. Thus, there can be a β-eliminatable substituent at the 5α-position, for example a halogen atom such as a chlorine or bromine atom, or an aromatic sulphonyloxy group such as a tosyloxy group. The β-eliminatable substituent can be eliminated by treatement with acid.

Where the grouping Y is a grouping convertible to a ketone function and a 3-keto compound is ultimately required, the conversion may be effected after introduction of the hemiacetal grouping. Thus, for example, a 3-ketal or 3-acetal may be subjected to acid hydrolysis or a 3-acyloxy group may be hydrolysed to a hydroxy group followed by oxidation to the required ketone. The oxidation may be effected for example, using a chromium trioxide oxidising agent.

One particularly useful method is to use intermediates having an acyloxy group in the 3-position and a β-eliminatable substituent at the 5α-position. After hemiacetal formation according to the process of the invention, hydrolysis followed by oxidation under acid conditions yields the desired Δ$^4$-3-keto structure.

The oxime of formula II may be prepared by photolysis of a nitrite of the skeletal formula

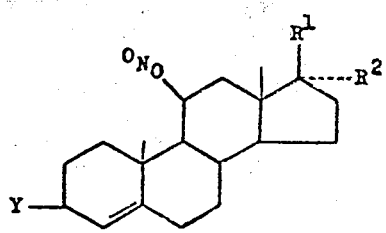

in ketone-protected form, by irradiation with UV light of a wavelength absorbed by the nitrite group. The photolysis may be effected in solution in an inert solvent, preferably one which does not absorb any of the photolysing radiation. The nitrite starting material may be prepared by reaction of the corresponding 11-hydroxy compound with a nitrosylating reagent e.g. a nitrosyl halide such as nitrosyl chloride. The reaction is advantageously effected in the presence of an acid binding agent e.g. a tertiary base such as pyridine. Where a further OH group is present, as in the 17β-hydroxy compounds, this will also be nitrosylated but due to the low reactivity of the 11-nitrito group, the unwanted additional nitrito group can be removed selectively by solvolysis; thus, for example, the 11β, 17β-bis-nitrito compound can be converted to the 11-nitrito-17-hydroxy compound simply by heating in a lower alkanol such as methanol.

The corresponding compounds having a β-eliminatable substituent at the 5α-position can be prepared in like manner by irradiation of the corresponding nitrite.

The 11-hydroxy compound can be prepared by reduction of the corresponding 11-one, e.g. using a metal hydride reducing agent such as sodium borohydride or lithium aluminium hydride.

Where compounds are required in which R$^2$ is hydroxyl and R$^1$ is an aliphatic group, this grouping at the 17-position can be introduced by reacting the corresponding 17-one with an appropriate organo-metallic compound such as a Grignard reagent or, in the case of the ethynyl compounds, an alkali metal acetylide. The introduction of such a grouping may be effected conveniently before reduction of the 11-one, e.g. by reacting the corresponding 11,17-dione with the appropriate reagent. The ethynyl group is conveniently introduced by passing acetylene into a solution of the dione in an inert solvent following by addition of an alkali metal t-alkoxide.

For the better understanding of the invention, the following Examples are given by way of illustration only; all temperatures are in °C:

EXAMPLE 1 a. $\Delta^5$-Androstene-11,17 dione-3 monoketal.

The $\Delta^4$-Androstene-3,11,17-trione (9g.) was heated at reflux with 2-methyl-2ethyl dioxolane (160 cc) and p-toluenesulfonic acid (150 mg.). Butanone (100 cc) was slowly, fractionally distilled over a period of 5.5 hours. The residue was diluted with benzene which was then washed with sodium bicarbonate and water, dried, and evaporated in vacuo. Crystallization from aqueous methanol gave 7.3 g. (70%) of the desired monoketal, m.p. 189°–94°C.

The analytical sample (methylene chloride-ether) had m.p. 194°–197°; $[\alpha]_D^{24}$ + 55°; $\mu_{max}^{KBr}$ 1735(vs), 1705(vs), 1670(w) cm.$^{-1}$ Anal. Calcd. for $C_{21}H_{28}O_4$: C, 73.21; H, 8.19; O, 18.58. Found: C, 73.49; H, 7.98; O, 18.62.

(b) 17$\alpha$ Ethynyl, 17$\beta$ hydroxy-$\Delta^5$ androsten-11-one-3 monoketal.

A solution of the monoketal prepared in (a) above (7 g.) in dry 3:2 benzene-ether (450 cc) was stirred and flushed with $N_2$. Then a slow stream of acetylene (purified through $H_2O$ and $H_2SO_4$) was passed into the reaction mixture for a total of 4 hours. After the first hour, potassium tertiary amylate (prepared by heating at reflux potassium (7g.)) in freshly distilled t-amyl alcohol (225 cc) until the metal dissolved) was added rapidly. At the end of the 4 hours, the reaction mixture was flushed with $N_2$. It was diluted with 2:3 benzene-ether (1.1). Small portions of saturated aqueous ($NH_4Cl$ (500 cc) were added. After separation of the phases, the aqueous layer was extracted with 1:1 benzene-ether and with ether. The organic layer was washed with water until colorless washes were obtained. Then the solution was dried and evaporated on the roto vac. Crystallization from aqueous methanol gave 7.2 g. (96%)

The analytical sample (methylene chloride-ether) had m.p. 236°–242°, $[\alpha]_D^{19}$ − 71.7° (c 1.74); $\mu_{max}^{KBr}$ 3590(m), 3330(s) 2125(w), 1710(vs), 1670(w) cm$^{-1}$ Anal. Calcd. for $C_{23}H_{30}O_4$: C, 74.54; H, 8.16; O, 17.28.

C, 74.53; H, 8.17; O, 17.51.

c. 17$\alpha$ Ethynyl-11$\beta$, 17$\beta$ dihydroxy-$\Delta^5$-androstene-3monoketal.

The 11-one from (b) above (4.5 g.) in methanol (215 cc) was treated with sodium borohydride (5 g.) in water (63 cc) and 1% sodium hydroxide in methanol (75 cc). The reaction mixture was heated at reflux overnight. The addition of water and saturated aqueous sodium chloride gave platelets of the desired 11$\beta$ hydroxy compound. Crystallization from methylene dichloride/methanol gave in three crops a total of 2.9 g. (64.5%).

$\mu_{max}^{KBr}$ 3700(m), 3600(s), 3400(m) 1100(vs) cm$^{-1}$
$[\alpha]_D^{24.5°}$ − 9.25° (0.830 - $CHCl_3$).

Anal. Crystallized from methylene dichloride/methanol (dried at 100° in vacuo for 3 days) - prisms - m.p. 255°–8°C.

$C_{23}H_{32}O_4$ requires: C, 74.16; H, 8.66; O, 17.18. Found: C, 73.89; H, 8.70.

d. 17$\alpha$-Ethynyl-androst-5-ene-11$\beta$,17$\beta$-diol-3-one-3-monoethylene ketal-11$\beta$-nitrite.

A solution of 17$\alpha$-ethynyl-androst-5-ene-11$\beta$,17$\beta$-diol-3-one-3 monoethylene ketal (4g.) in pyridine (Fisher reagent grade; 60 ml.) was treated with excess of nitrosylchloride at ca. 50° until the solution became reddish brown. Dilution with ice-water, extraction with methylene dichloride and evaporation of the solvent in vacuo at ca. 45° (bath-temperature) gave the crude 11$\beta$, 17$\beta$-bis-nitrito compound, which without further purification was refluxed with methanol for ca. 1 hour. The course of the reaction could be best followed by disappearance of the starting material by TLC (Thin Layer Chromatography). The 11-nitrite group mostly survived such solvolysis. Evaporation of the solvent in vacuo at ca. 45° (bath-temperature) gave a crude crystalline residue. Chromatography of the same in methylene dichloride over neutral alumina (20g.) and elution with the same solvent (ca. 125 ml.) gave the crystalline 11-mononitrite, which was triturated with large excess of hexane and set aside in the cold. Filtration gave the desired crystalline 11-mononitrite (3.6g., 83.5%) m.p. 168°–174°. Recrystallization from methylene dichloride gave prisms, m.p. 171°–174°, $[\alpha]_D^{24.5°}$ − 81.38° (c 0.98 in chloroform); $\mu_{max}^{KBr}$ 3550 (s) 3360(m), 1640(vs) and 1600(m) cm.$^{-1}$ Anal. Calcd. for $C_{23}H_{31}O_5N$: C, 68.80; H, 7.78; O, 19.93; N, 3.49.

Found: C, 68.93; H, 7.62; O, 19.79; N, 3.60.

e. 17$\alpha$-Ethynyl-19-oximino-androst-5-ene-11,$\beta$,17$\beta$-diol-3one-3-monoethylene ketal.

i. A solution of the 11-mononitrite prepared in d) above (1.2 g.) in dry benzene (170 ml.) was irradiated at 6–10° (bath-temperature) with a 200 watt mercury arc lamp for 57 minutes (disappearance of the nitrite spot on TLC) in a pyrex vessel.

After evaporation of the solvent under reduced pressure, the residue was chromatographed over neutral alumina (28 g.). Elution with methylene dichloride containing increasing proportions of methanol gave the following compounds in order of each of elution: (I) 17$\alpha$-ethynyl-androst-5-ene-17$\beta$-ol-3,11-dione-3-monoethylene ketal (140 mg.); (II) 17$\alpha$-ethynyl-androst-5-ene-11$\beta$,17$\beta$-diol-3-one-3 monoethylene ketal (35 mg.); (III) trace oil fractions consisting mainly of 11-alcohol 19-oxime and some compound of intermediate polarity; (IV) the desired 19-oxime (437 mg, 36.4%) m.p. 215°–220° as white powder. Recrystallization (with difficulty) from methylene dichloride hexane gave micro crystals, m.p. 224°–227°; $[\alpha]_D^{26}$ − 154° (c 0.487 in dioxane) $\mu_{max}^{KBr}$ 3510(vs), 3360(vs), 1650(vw), 1095(vs) cm.$^{-1}$ A sample has been sent for analysis.

Anal. Calcd. for $C_{23}H_{30}O_5N$: C, 68.98; H, 7.55; O, 19.98; N, 3.50. Found: C, 68.53; H, 7.62; O, 20.27; N, 3.61.

ii. A solution of the 11-mononitrite prepared in Example 1 (4g.) in dry benzene (750 ml.) was photolyzed as in (a) above with a 550 watt lamp for 36 minutes, during which time the reaction was virtually complete (TLC). After evaporation of the solvent, the light-brown residue was dissolved in methylene dichloride (40 ml.), seeded with 19-oxime (from the previous batch) and allowed to stand overnight at room temperature. Crystallization ensued in ca. 30 minutes. The white ppt. was filtered off, washed with methylene dichloride (ca. 20 ml.) and dried in air. This still contained some less polar impurities (TLC) and was hence warmed with methylene dichloride (25 ml.) to give a suspension and filtered after letting it stand overnight at room temperature. The residue (1.88 g., 47%), m.p. 215°–222°, $[\alpha]_D^{26} - 152.6°$ (c 0.51 in dioxane), was almost pure 19-oxime as shown by TLC. Its infra-red spectrum was almost identical with that of the analytical specimen.

f. 17α-Ethynyl-19-oxo-androst-5-ene-11β,17β-diol-3-one-11, monoethylene ketal-11,19-hemiacetal The 19-oximino compound produced in (e) above (1.13g.) in glacial acetic acid (79 ml.) and water (40 ml.) was treated with sodium nitrite crystals (2.8 g.) and kept at room temperature for ca. 15 min. The crude crystalline product obtained on dilution with water and extraction with methylene chloride, was dissolved in methanol (45 ml.) and treated with methanolic sodium hydroxide (68 ml., 10%) at R.T. After 3 hrs. the reaction product was neutralized with dilute hydrochloric acid and the solvents removed in vacuo. Trituration with water gave prisms (855 mg., 78.3%), m.p. 270°–274°. After crystallization from methanol-methylene chloride, this had m.p. 272°–277°, $[\alpha]_D^{23} + 12.5°$ (c 0.74 in dioxan); $\mu_{max}^{KBr}$ 3670(vs), 3360(s), 2130(vw), 1660(w), 1110(s) cm.$^{-1}$ Anal.Calcd. for $C_{23}H_{30}O_5$: C, 71.45; H, 7.82; O, 20,69 Found: C, 71.45; H, 7.69; O, 20.80 g. 17α-Ethynyl-19-oxo-androst-4-ene-11β,17β-diol-3-one-11,19-hemiacetal

The above ketal (1.2 g.) was taken up in dioxan (77 ml.) containing aqueous hydrochloric acid (8.1 ml., IN) and left at R.T. for ca. 24 hr. Dilution with saturated brine, extraction into methylene chloride and crystallization from benzene-hexane gave the crude compound (916 mg., 80%) as amorphous powder, m.p. 115°–130°, $\lambda_{max}$ 246mµ ($\epsilon$ 10,500). T.L.C. analysis (silica gel plate impregnated with fluorescein, 6% methanol in methylene chloride, developed with phosphomolybdic acid) showed a slight non-U.V.-absorbing Δ$^5$-3-ketone just ahead of the U.V.-absorbing spot corresponding to the desired Δ$^4$-3-ketone. Purification was difficult to effect by crystallization. However, an analytical sample (benzene-hexane) had m.p. 120°–132°, $[\alpha]_D^{18} + 110.1°$ (c 0.445) $\lambda_{max}$ 247mµ ($\epsilon$ 11,000).

Anal. Calcd. for $C_{21}H_{26}O_4$: C, 73.65; H, 7.67; O, 18.69. Found: C, 73.54; H, 7.80; O, 18.58.

The presence of unconjugated ketone does not effect the biological activity and the crude product described above may be used directly in medical applications.

EXAMPLE 2 a. 11β-Nitrosylprogesterone 3,20-Bisketal.

Excess nitrosyl chloride was passed through a solution of 4g. of 11β-hydroxyprogesterone 3,20-bisketal in 40 ml. of pyridine at 40°. Ice was added, followed by water, to precipitate the crude nitrite. The product was crystallized from hexane; m.p. 130°–134°, $[\alpha]_D^{24} + 5°$. Compound was unstable and satisfactory analytical data were not obtained; $\mu_{max}^{KBr}$ 2995(s), 1625(s), 1600(m) cm.$^{-1}$ (ONO): yield 77% b. 18-Oximino-11β-hydroxyprogesterone 3,20-Bisketal

A solution of 10 g. of nitrite from (a) above in 300 ml. of toluene was irradiated for 1.5 hr. using a 200-w. mercury vapor lamp. The toluene was removed under reduced pressure; the derived 18-oxime was precipitated with ethyl acetate and recrystallized from the same solvent; m.p. 263°–265°; $[\alpha]_D^{20} - 23°$; $\mu_{max}^{KBr}$ 3300(s), (OH), 2995(s), 1650(w) cm.$^{-1}$ (C=N); yield 18%.

Anal. Calcd. for $C_{25}H_{37}NO_6$: C, 67.39; H, 7.92; N, 3.14. Found: C, 67.22; H, 8.14; N, 3.16.

c. 11,19-Hemiacetal of 11β-Hydroxy-19-oxoprogesterone 3,20-Bisketal

To 40 ml. of cold glacial acetic acid was added 2 g. of sodium nitrite followed by the mother liquors from (b) containing the 19-oxime. The mixture was stirred for 2.5 min. at 5°. After the usual work-up, the resulting oil was taken up in 30 ml. of 1% methanol-sodium hydroxide. Upon standing, the product crystallized from the reaction mixture; m.p. (recrystallized from methanol) 245°–256°; $[\alpha]_D^{23} + 52°$; $\mu_{max}^{KBr}$ 3700(s) (OH), 3000(s) cm.$^{-1}$; yield 74%.

Anal. Calcd. for $C_{25}H_{36}O_6$: C, 69.42; H, 8.39.
Found: 68.92, H, 8.46.

d. 11,19-Hemiacetal of 11 -Hydroxy-19-oxoprogesterone and Its Δ$^{5,6}$ Isomer

A suspension of 115 mg. of the 11,19-hemiacetal bisketal from (c) above in 4.5 ml. of acetone and 1.25 ml. of water containing 0.05 ml. of concentrated sulfuric acid was heated under reflux for 15 min. to effect solution and allowed to stand at room temperature for an additional 30 min. After the usual work-up, a mixture of the products was obtained from methanol; m.p. 210°–222°, $[\alpha]_D^{24} + 227°$; $\lambda_{max}^{MeOH}$ 246mµ ($\epsilon$7800); $\mu_{max}^{KBr}$ 3600(s) (OH), 3000(s), 1715(s) (20–C=O), 1693(s) (β,γ-unsaturated C=O), 1660(s), 1610(m) cm.$^{-1}$ (C=C-C=O); yield 99%.

Anal. Calcd. for $C_{21}H_{28}O_4$: C, 73.23; H, 8.19. Found: C, 72.94; H, 8.05.

On treatment with HCl in aqueous dioxane the above mixture was converted to nearly pure Δ$^4$-3-keto compound.

We claim:

1. A method of contraception whereby at least one steroid hemiacetal of the skeletal formula:

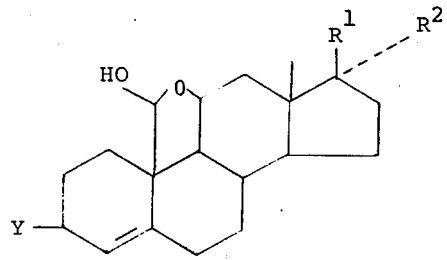

(where Y is a ketone oxygen atom or represents a grouping convertible thereto, R$^1$ is a group COCH$_2$X, where X is a hydrogen or halogen atom, and R$^2$ is a hydrogen atom or an acyloxy group or R$^1$ is a hydroxy group and R$^2$ is an aliphatic group which may carry one or more halogen atoms as substituents and where the 6β-, 9α- and 16-positions carry hydrogen atoms or substituents selected from the group consisting of a halogen atom or an alkyl group at the 6β-position, a halogen atom at the 9α-position, or a methyl or methylene group, a halogenated methyl or methylene group or a halogen atom at the 16-position) is administered orally to a human subject.

2. A method as claimed in claim 1 in which R$^2$ is a methyl, vinyl or ethynyl groups or a chlorovinyl group.

3. A method as claimed in claim 1 in which R$^1$ is an acetyl group.

4. A method as claimed in claim 1 in which Y is ketonic oxygen, $R^1$ is a hydroxy group and $R^2$ is an ethynyl group.

5. A method as claimed in claim 1 in which the active substance of formula I is administered at a daily dose level of 1 to 25 mg per day.

6. A method as claimed in claim 1 in which the active substance of formula I is administered at a daily dose level of 2 to 10 mg per day.

* * * * *